United States Patent [19]
Hoffheins et al.

[11] Patent Number: 5,451,920
[45] Date of Patent: Sep. 19, 1995

[54] THICK FILM HYDROGEN SENSOR

[75] Inventors: Barbara S. Hoffheins, Knoxville; Robert J. Lauf, Oak Ridge, both of Tenn.

[73] Assignee: Martin Marietta Energy Systems, Inc., Oak Ridge, Tenn.

[21] Appl. No.: 170,628

[22] Filed: Dec. 20, 1993

Related U.S. Application Data

[63] Continuation-in-part of Ser. No. 957,337, Oct. 6, 1992, Pat. No. 5,367,283.

[51] Int. Cl.$^6$ ................................................ H01C 7/00
[52] U.S. Cl. ........................................ 338/34; 338/307; 338/320
[58] Field of Search ................. 338/34, 320, 35, 306, 338/307; 204/424, 426, 428, 431; 427/125; 422/90; 501/19

[56] References Cited

U.S. PATENT DOCUMENTS

| | | | |
|---|---|---|---|
| 3,559,457 | 2/1971 | Collins | 73/23 |
| 4,624,137 | 11/1986 | Johnson et al. | 73/204 |
| 4,908,118 | 3/1990 | Ammende et al. | 204/424 |
| 4,976,991 | 12/1990 | Ammende et al. | 427/125 |
| 5,338,708 | 8/1994 | Felten | 501/19 |

OTHER PUBLICATIONS

P. A. Michaels, "Summary Report: Design, Development and Prototype Fabrication of an Area Hydrogen Detector (5 Apr. 1963 through 4 Apr. 1964)," Sep. 1964.

P. J. Shaver, "Bimetal Strip Hydrogen Gas Detectors," *The Review of Scientific Instruments*, vol. 40, No. 7, pp. 901–905, Jul. 1969.

M. A. Butler and D. S. Ginley, "Hydrogen Sensing with Palladium-Coated Optical Fibers," *J. Appl. Phys.*, 64(7), pp. 3706–3712, 1 Oct. 1988.

*Primary Examiner*—Marvin M. Lateef
*Attorney, Agent, or Firm*—Joseph A. Marasco; J. Donald Griffin; Harold W. Adams

[57] ABSTRACT

A thick film hydrogen sensor element includes an essentially inert, electrically-insulating substrate having deposited thereon a thick film metallization forming at least two resistors. The metallization is a sintered composition of Pd and a sinterable binder such as glass frit. An essentially inert, electrically insulating, hydrogen impermeable passivation layer covers at least one of the resistors.

20 Claims, 7 Drawing Sheets

THICK FILM HYDROGEN SENSOR

The United States Government has rights in this invention pursuant to contract no. DE-AC05-84OR21400 between the United States Department of Energy and Martin Marietta Energy Systems, Inc.

CROSS REFERENCE TO RELATED APPLICATION

This application is a continuation-in-part of application Ser. No. 07/957,337, filed on Oct. 6, 1992, U.S. Pat. No. 5,367,283, issued on Nov. 22, 1994, entitled Thin Film Hydrogen Sensor, the entire disclosure of which is incorporated herein by reference.

FIELD OF THE INVENTION

The present invention relates to devices and methods for monitoring the composition of gases and, more particularly, to solid state devices incorporating palladium (Pd) metal films, and methods relating thereto for measuring hydrogen concentration in a gas composition.

BACKGROUND OF THE INVENTION

In the field of gas sensing and analysis, it is well known that when Pd metal is exposed to hydrogen gas, hydrogen molecules dissociate on the Pd surface and the resulting hydrogen atoms can diffuse into the bulk of the Pd, eventually reaching an equilibrium concentration in the metal. It is therefore possible to measure the gaseous concentration of hydrogen by measuring one or more of the physical properties of Pd that are influenced by dissolved hydrogen.

Known methods include measurement of the physical expansion of a known length of Pd rod (R. L. Collins, Hydrogen Detector, U.S. Pat. No. 3,559,457), the deflection of a bimetallic strip (P. J. Shaver, Bimetal Strip Hydrogen Gas Detectors, The Rev. of Sci. Instru. 40 [7], 901–5, 1969), and the elongation of a Pd-coated optical fiber (M. A. Butler and D. S. Ginley, Hydrogen Sensing with Pd-Coated Optical Fibers, J. Appl. Phys. 64 [7], 3706–12, 1988).

Another technique is to measure changes in the electrical resistivity of a Pd thin film (P. A. Michaels, Design, Development, and Prototype Fabrication of an Area Hydrogen Detector, Bendix Corporation, Southfield, Mich., 1964, Contract NAS8-5282). Because the resistance changes are small, it is necessary to amplify the signal and, at the same time, to provide temperature compensation. Michaels, therefore, used two rectangular Pd thin films, deposited side-by-side on a glass slide. The film dimensions were such that each strip had a resistance of about 10 $\Omega$. One strip was covered by a thin layer of silicone resin or Mylar tape, and the other was uncovered. An external circuit was constructed such that the two strips formed the passive and active legs, respectively, of a Wheatstone resistance bridge.

The hydrogen sensor described by Michaels had several limitations. Firstly, the Pd was deposited directly onto the glass substrate, and adhesion thereto was not sufficient for use in a practical device, particularly at high hydrogen concentrations. High concentrations of hydrogen generally lead to appreciable mechanical strain in the Pd film and cause it to peel away from the substrate.

Moreover, the two-element bridge required external bridge resistors and cumbersome electronics which would make a practical device more difficult to produce. The external resistors very often are variable resistors so that one can adjust them to bring the bridge into balance at some reference condition (e.g., to give a zero reading when no hydrogen is present). These external circuits are usually cumbersome and a source of noise in the output signal.

Furthermore, when the active and passive metallizations are configured as two parallel rectangles, their resistance is generally undesirably low in a sensor of any practical size. This in turn requires either a large current in the bridge or a very sensitive amplifier.

Further still, the low aspect ratio of the Pd strips (L/W$\cong$10) and their correspondingly low resistance (10 $\Omega$) leads to high power consumption and inefficient amplification, which would make a practical device more difficult to operate.

Finally, the use of polymer films as the passivation layer is incompatible with high temperature or hostile environment applications, severely limiting the usefulness of a practical device.

OBJECTS OF THE INVENTION

Accordingly, among the objects and advantages of the present invention is the provision of a new and improved hydrogen detecting device having a thick film Pd hydrogen sensing element with enhanced adhesion and robustness. The device is lightweight and portable, exhibits low power consumption, is capable of functioning at relatively high concentrations such as the explosive limit in air (4%), is useful in hostile environments and at high temperatures, and exhibits an improved signal-to-noise ratio.

Further and other objects and advantages of the present invention will become apparent from the description contained herein.

SUMMARY OF THE INVENTION

According to one aspect of the invention, a hydrogen sensor element comprises an essentially inert, electrically-insulating substrate having deposited thereon a thick film metallization forming at least two resistors. The metallization is a sintered composition of Pd and a sinterable binder such as glass frit. An essentially inert, electrically insulating, hydrogen impermeable passivation layer covers at least one of the resistors.

According to another aspect of the invention, a hydrogen sensor element comprises an essentially inert, electrically-insulating substrate having deposited thereon a thick film metallization forming four resistors in a Wheatstone resistance bridge arrangement. The metallization comprises a sintered composition of Pd-Ag alloy and glass frit. An essentially inert, electrically insulating, hydrogen impermeable passivation layer covers at least one of the resistors.

According to a further aspect of the invention, an apparatus for detecting hydrogen comprises a hydrogen sensor element in resistance bridge arrangement as herein above described. A power supply means for applying a fixed voltage to the resistance bridge, and a measuring means for detecting and measuring a voltage imbalance of the resistance bridge are connected electrically thereto.

According to a still further aspect of the invention, a method of making a thick film hydrogen sensor comprises the steps of:

(a) providing an essentially inert, electrically-insulating substrate;

(b) depositing on the substrate a thick film metallization precursor, comprised of a composition of Pd and a sinterable binder, which forms at least two resistors on the substrate;

(c) sintering the metallization precursor to form a metallization; and, (d) depositing on the substrate an essentially inert, electrically insulating, hydrogen impermeable passivation layer covering at least one of the resistors.

For a better understanding of the present invention, together with other and further objects, advantages and capabilities thereof, reference is made to the following disclosure and appended claims in connection with the above-described drawings.

DETAILED DESCRIPTION OF THE INVENTION

Figure 1:
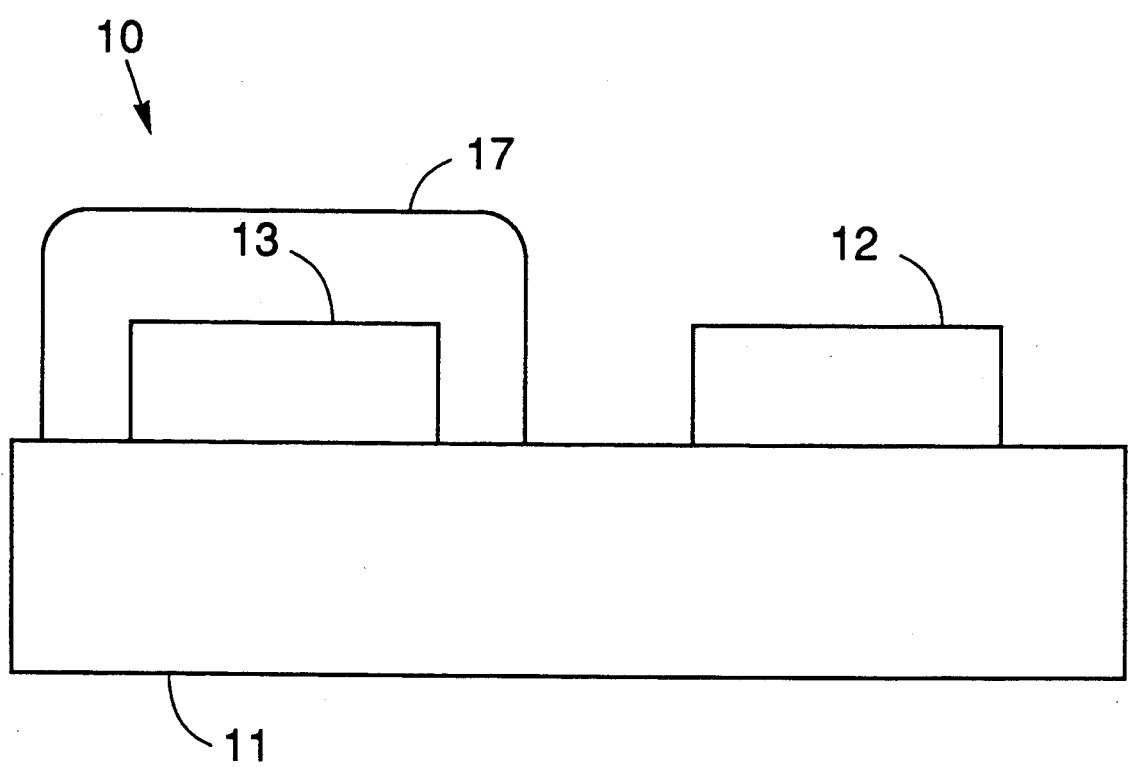
FIG. 1 is a schematic cross sectional side view showing the layers of a hydrogen sensing element having two thick film metallizations on an inert substrate; one metallization is covered and the other metallization is exposed.

Referring firstly to FIG. 1, in a preferred embodiment of the present invention, a simplified hydrogen sensor element 10 comprises thick film metallizations 12, 13 deposited on a relatively inert substrate 11 comprised of silicon, glass, quartz, mica, ceramics, or porcelain. The thick film metallizations 12, 13 are easily deposited on the substrate 11 using well known, conventional techniques such as screen printing and direct writing. A layer of sinterable (sinterable and/or fusible) paste or ink, referred to hereinafter as a precursor, is applied to the substrate 11 and sintered (fired to the point of sintering and/or fusing) to obtain a strongly adherent metallization layer on the substrate 11. Thickness values set forth herein refer to nominal, after-sintering values determined from precursor manufacturer's specifications.

The precursor is generally comprised of a metal powder comprising Pd or Pd alloy and about 1–10% (by weight) of a sinterable inorganic binder material such as glass frit. Glass frit usually comprises a powdered composition of silica and an oxide of at least one of the following elements: Al, B, Ba, Ca, Mg, Zn, Pb, and Ti. The precursor usually also contains about 5–10% of an organic binder such as a modified cellulose and plasticizer, and about 10–30% of an organic solvent. An example of a suitable precursor is a mixture of about 50% Pd or Pd-Ag alloy powder, about 5% modified lead borosilicate glass frit, about 10% ethyl cellulose, and about 30% terpineol. (Lead borosilicate glass frit can be conventionally modified to improve properties by adding small amounts of various oxides.) The sintered metallization may contain pure Pd or an alloy thereof; Pd-Ag alloys containing up to about 15% Ag are particularly suitable for some applications because the Ag content tends to mitigate volume expansion problems at high hydrogen concentrations. A suitable precursor composition is DuPont 7150D, a thick film precursor material available from the DuPont Company, Wilmington, Del. Other suitable precursor compositions are described hereinbelow.

A hydrogen-impermeable passivating layer 17 is deposited in a pattern large enough to completely cover the top and edges of the covered metallization 13 in order to prevent hydrogen absorption thereby. The passivating layer 17 can be any essentially inert, electrically insulating material, usually a ceramic, characterized by low permeability to hydrogen, that can be deposited in a layer having adequate thickness and density. The passivating layer 17 can be deposited by any suitable conventional technique such as sputtering or chemical vapor deposition, preferably by a conventional thick film deposition technique wherein a precursor of the same or similar composition as the metallization precursor, but with no metal content, is deposited on the metallization 13 and sintered to obtain a strong, adherent hydrogen impermeable layer.

During exposure to analyte gases, the resistance of the uncovered, exposed metallization 12 is compared to that of a covered, unexposed metallization 13 in order to eliminate the effects of temperature changes on resistivity. The resistance difference between the exposed metallization 12 and unexposed metallization 13 can be easily measured. The familiar Wheatstone Bridge technique is preferred, wherein an imbalance in the resistance bridge is measured.

Figure 2:
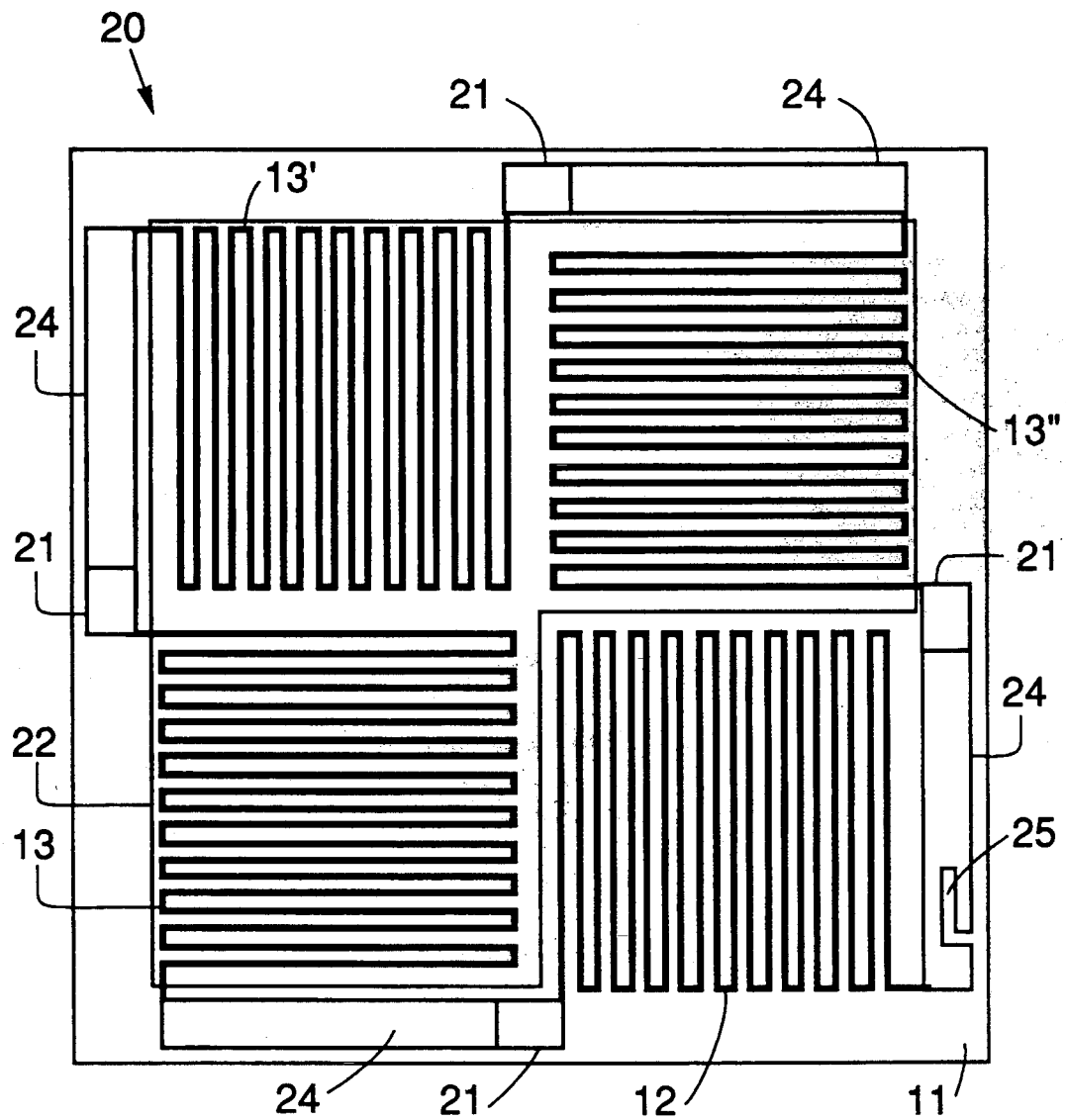
FIG. 2 is a plan view of a hydrogen sensing element having a bridge circuit comprising four sinuous resistors, three of which are covered by a passivating layer.

Referring now to FIG. 2, in a preferred embodiment of the present invention, a practical sensor element 20 incorporates all four resistor legs of a Wheatstone resistance bridge (one uncovered metallization 12 and three identical covered metallizations 13, 13', 13") deposited as described hereinabove, and having deposited thereon a single passivating layer 22 covering the covered metallizations 13, 13', 13". The single passivating layer 22 is shown in FIG. 2 as a border outline in order to illustrate clearly all aspects of the covered metallizations 13, 13', 13". Large interconnective elements 21 are provided for ease in connecting the sensor element 20 to other components in a detecting instrument. The interconnective elements 21 are preferably comprised of a composition which is compatible with the sensor material and has good solderability. A very suitable composition is DuPont 6120, a thick film precursor material available from DuPont.

The sinuous pattern of the metallizations 12, 13, 13', 13" greatly increases their aspect ratios and electrical resistance. A suitable aspect ratio would be in the range of $L/W \simeq 100–1000$, preferably $L/W \simeq 200–800$, more preferably $L/W \simeq 300–700$, most preferably $L/W \simeq 400–600$. Specific aspect ratios and electrical resistance values are not critical to the practice of the invention, and these values can be varied by the skilled artisan for optimal performance under a given set of circumstances.

In a preferred embodiment, each of the metallizations 12, 13, 13', 13" has in series therewith a secondary resistive element 24 providing means for trimming the pattern by cutting lines 25 by laser, abrasion, or other means. In this way, the resistances of all four bridge resistors can be balanced during the manufacturing process, eliminating the need for external variable resistors.

It will be appreciated by those skilled in the art that the compositions and methods used to form the interconnective elements 21 and secondary resistive elements 24 can be the same as that used to form the metallizations 12, 13, 13', 13", or, they can be different. All elements can be deposited together in one step, or, one or more types of elements can be deposited separately and then sintered together. Many variations can be made while remaining within the scope of the invention.

Figure 3:
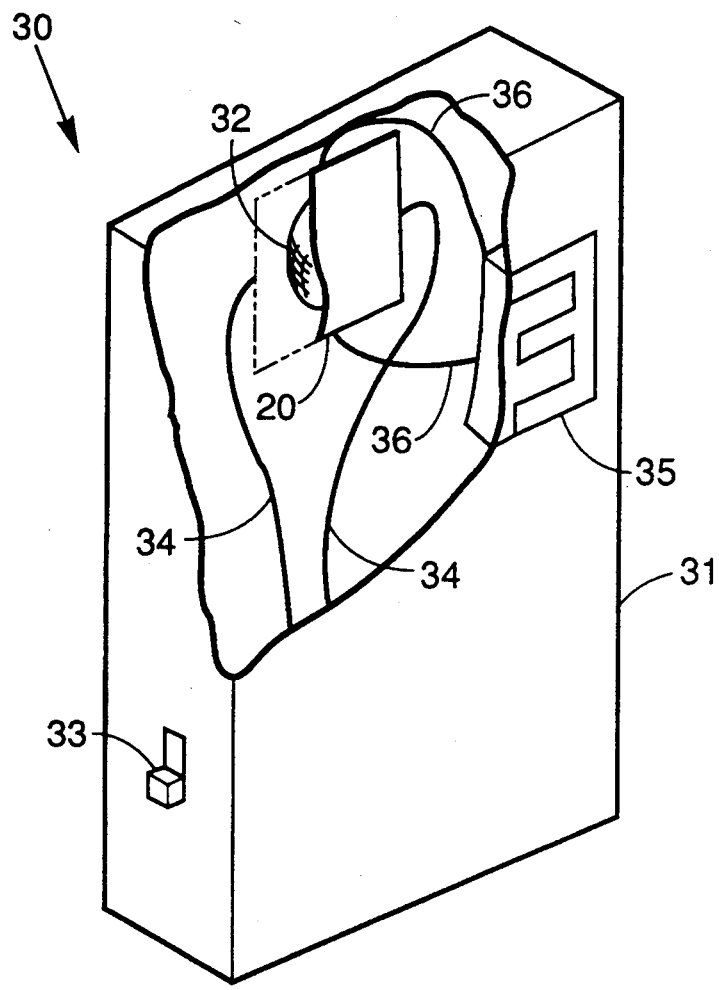
FIG. 3 is a cutaway oblique view of a portable, battery-powered hand-held hydrogen sensing apparatus showing the sensor element and digital voltage display.
Figure 4:
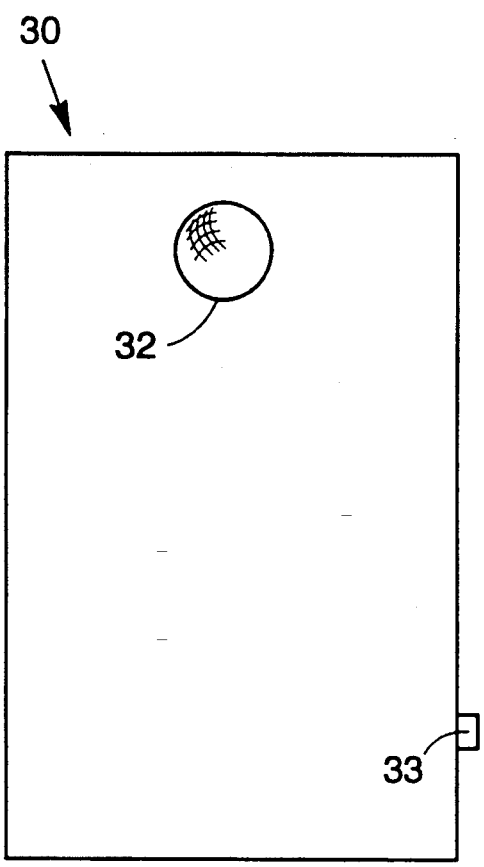
FIG. 4 is a rear view of the apparatus shown in FIG. 3.
Figure 5:
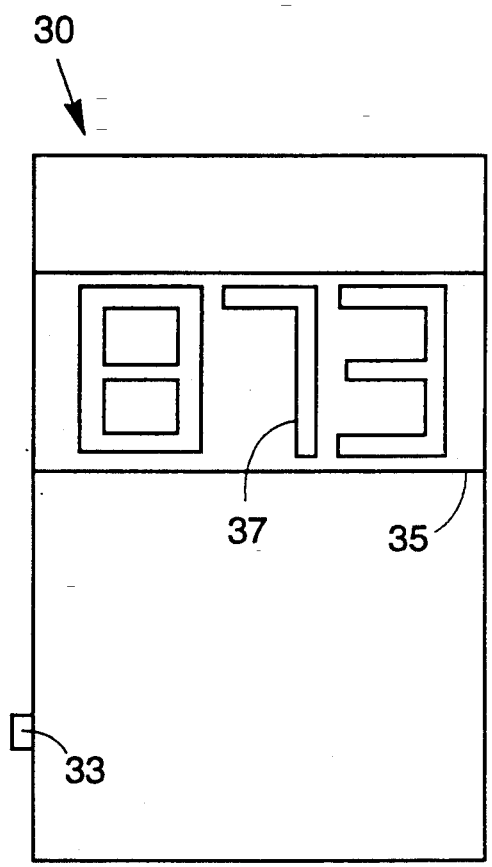
FIG. 5 is a front view of the apparatus shown in FIG. 3.

FIGS. 3, 4 and 5 show various views of a small, battery-powered hydrogen detector constructed in accordance with the present invention. Contained within a plastic or metal case 31, the hydrogen sensor element 20 is placed directly behind an opening 32 which is preferably covered with a wire mesh screen in order to protect the sensor element 20 and prevent ignition. Switch 33 is activated to apply voltage from a battery (normally 9 V, not shown) across the resistance bridge on the sensor element 20 through a first circuit formed by two wires 34. Orientation of the sensor element 20 is not critical as to the position of the resistor which is left uncovered for absorbing hydrogen. The voltage difference between the active and passive bridge elements on the sensor element 20 is measured by a digital voltmeter 35 through a second circuit formed by two wires 36, and thereby displayed digitally 37. Depending on the orientation of the sensor element 20, a positive or negative voltage difference will be measured.

EXAMPLE I

A sensor element having the metallization pattern shown in FIG. 2 was prepared by screen printing on a 1 inch square alumina substrate. Each layer was applied and fired separately. First, the interconnections 21 were applied using DuPont 6120 composition at a thickness of about 14 $\mu$m, and sintered for about 1 hour in a belt furnace, and at a peak temperature of about 850° C. for about 10 minutes. The metallizations 12, 13, 13', 13" were applied using DuPont 7150D composition at a thickness of about 25 $\mu$m, with a line width of 340 $\mu$m (L/W$\simeq$395), resulting in a nominal resistance of about 200 $\Omega$ per leg. The pattern was sintered as described hereinabove. The sintered pattern showed no appreciable distortion. The secondary resistive elements 24 were applied using DuPont 1711 composition at a thickness of about 25 $\mu$m and sintered as described hereinabove. The passivation layer 22 was applied using two layers of DuPont 9429 dielectric composition, at a total thickness of about 80 $\mu$m, each layer sintered separately as described hereinabove.

EXAMPLE II

A sensor element was prepared as described in Example I, with a difference in line width. A narrower line width of 250 $\mu$m (L/W$\simeq$860) was used, resulting in a nominal resistance of about 500 $\Omega$ per leg.

EXAMPLE III

A sensor element was prepared in similar fashion as described in Example II, with differences in precursors. The metallizations 12, 13, 13', 13" were applied using a mixture comprising DuPont 7150D composition and 22 wt. % Pd black (99.95% Pd, 0.1–0.3 $\mu$m particle size, available from Johnson-Matthey, Inc., Seabrook, N.H. The secondary resistive elements 24 were applied using DuPont 6120 composition at a thickness of about 25 $\mu$m and sintered as described in Example I. The passivation layer 22 was applied using two layers of DuPont 9137 resistor encapsulant composition, at a total thickness of 50 $\mu$m, each layer sintered for about 1 hour in a belt furnace, and at a peak temperature of about 525° C. for about 10 minutes.

EXAMPLE IV

Figure 6:
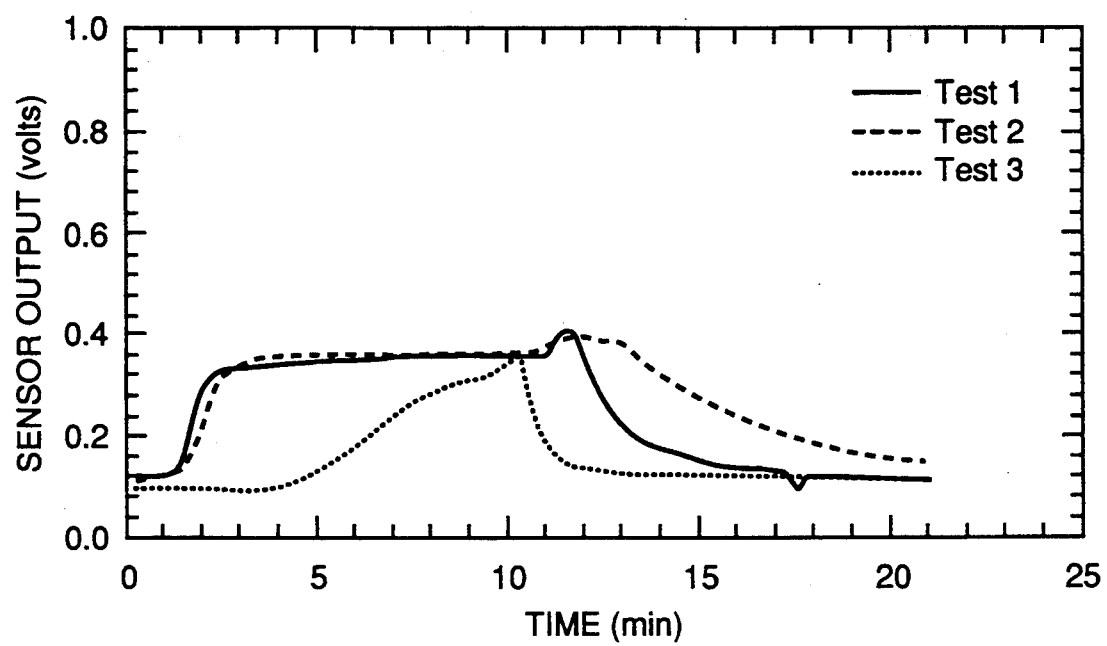
FIG. 6 is a graph showing the results of a test of one embodiment of the invention.

A sensor prepared as described in Example III was connected in Wheatstone bridge fashion to a 9 volt dc power supply and a computer equipped with an analog-to-digital interface. The sensor was placed in a gas flow chamber and sensor output in volts was monitored every 15 seconds during three trials. In each trial, readings were taken for 1 minute in ambient air (no gas flow) followed by flow of Ar-4%H$_2$. In the first trial, the flow of Ar-4%H$_2$ was stopped after 10 minutes. In the second and third trials, the flow of Ar-4%H$_2$ was stopped after 11 minutes. After stopping the flow of Ar-4%H$_2$, the chamber was opened to allow ambient air to quickly replace the Ar-4%H$_2$, and readings were taken for several minutes thereafter. Results of the three trials are shown in FIG. 6.

A DuPont experimental thick film precursor composition, designated 70179-142f, comprises 30–80% finely divided particles of Pd powder having a surface area of 3–10 m$^2$/g and density of 0.5–0.7 g/cc, and 2–10% finely divided particles of a glassy inorganic binder, dispersed in 68–10% of an organic solvent (medium). A patent application naming John J. Felten as inventor, entitled "Palladium Thick-Film Conductor" and assigned Docket No. EL-0378 by the Dupont Company, Wilmington, Del., is being filed on even date herewith. The 70179-142f composition is particularly useful for carrying out the present invention.

EXAMPLE V

A sensing element was prepared as described in Example III except that the metallizations 12, 13, 13', 13" were printed using the 70179-142f composition, sintered for about 1 hour in a belt furnace, and at a peak temperature of about 1000° C. for about 10 minutes. The passivation layer 22 comprised one layer of DuPont 9137 resistor encapsulant sintered for about 1 hour in a belt furnace, and at a peak temperature of about 525° C. for about 10 minutes. After all firings were complete, the resistances of metallizations, 12, 13, 13', 13" were all nominally about 75 $\Omega$, well within expected tolerances and within the range of adjustment available by trimming resistors 24.

EXAMPLE VI

Figure 7:
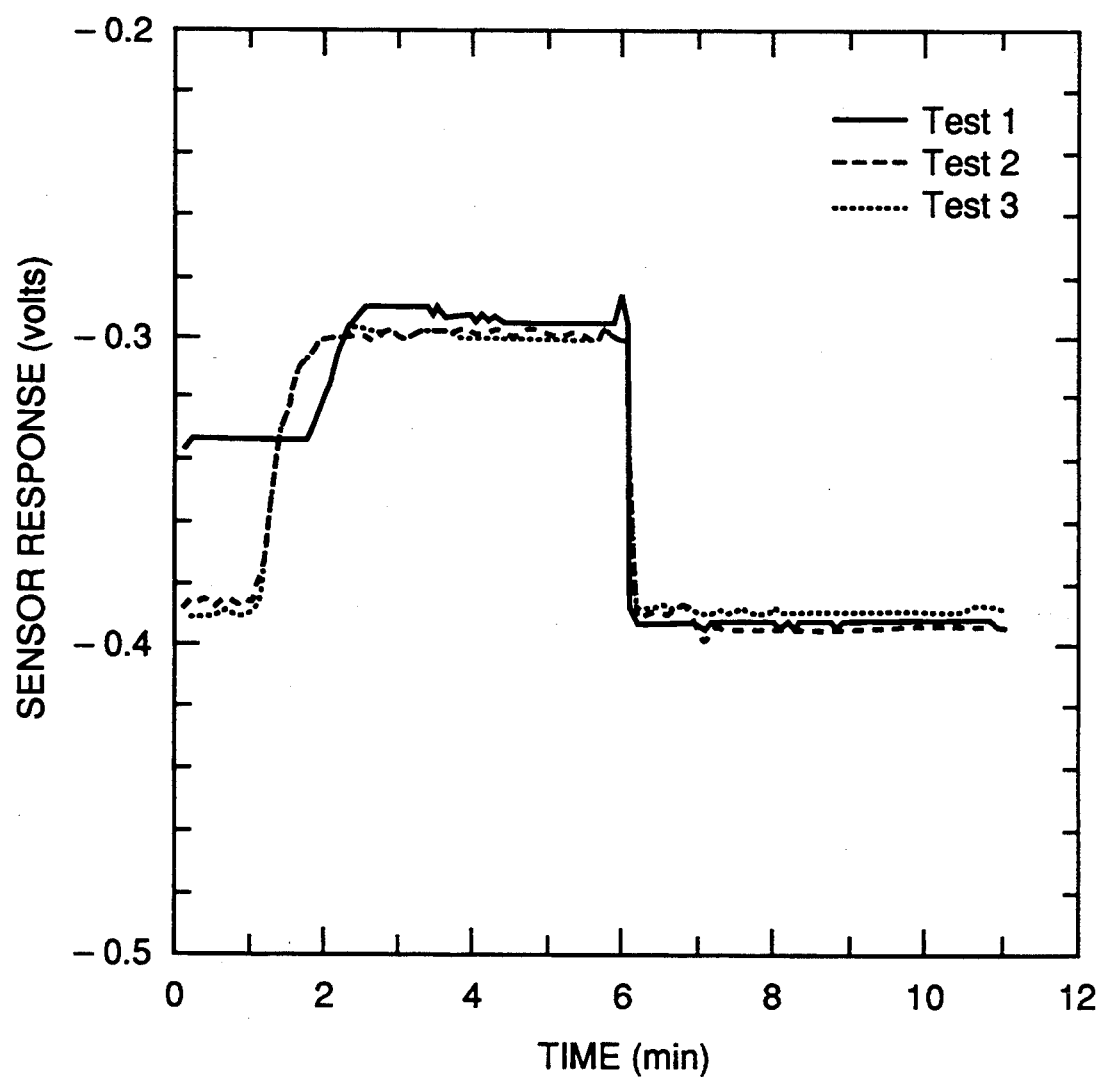
FIG. 7 is a graph showing the results of a test of another embodiment of the invention.

A sensing element prepared as described in Example V was tested as described in Example IV except that readings were made every 5 seconds for the duration of the test. The sensor response is shown in FIG. 7 in which it can be seen that the sensor is responsive to 4% hydrogen in argon at room temperature; the response improved after the first test.

EXAMPLE VII

A sensing element was prepared as described in Example V except that the passivation layer 22 covered only two of the metallizations, 13 and 13'. After all firings were complete, the resistances of metallizations, 12, 13, 13', 13" were all nominally 75 Ω, well within expected tolerances and within the range of adjustment available by trimming resistors 24.

EXAMPLE VIII

Figure 8:
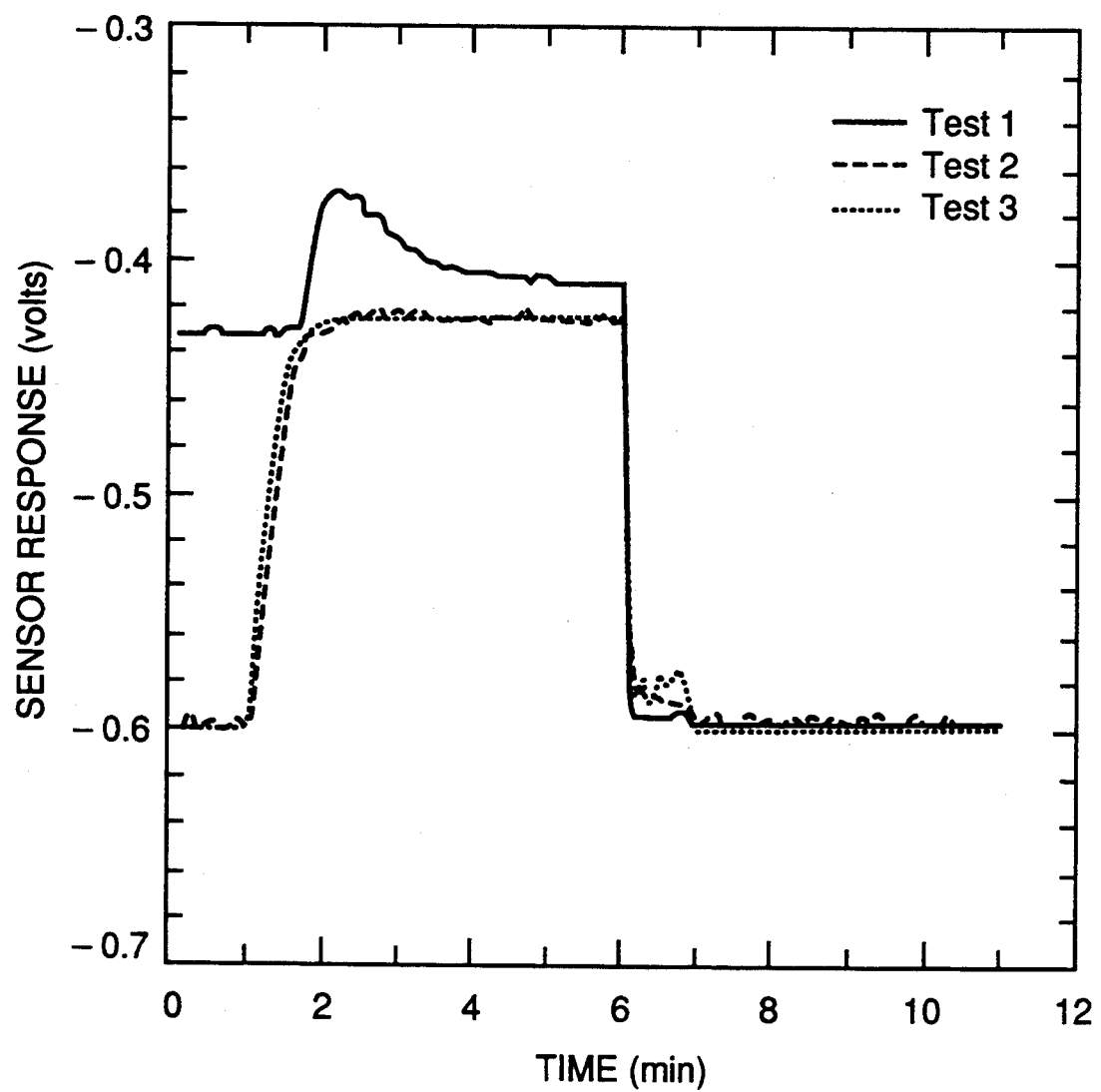
FIG. 8 is a graph showing the results of a test of yet another embodiment of the invention.

A sensing element prepared as described in Example VII was tested as described in Example VI. The sensor response is shown in FIG. 8 in which it can be seen that the sensor is responsive to 4% hydrogen at room temperature; the response improved after the first test. With two of the metallizations uncovered, sensor response to the 4% hydrogen was two times the output of the single uncovered metallization of the sensor in Example V, as expected.

EXAMPLE IX

A hydrogen detecting instrument is constructed as shown in FIGS. 3, 4, and 5. The entire instrument is contained within a conventional plastic case having nominal dimensions of about $3 \times 5\frac{1}{2} \times 1\frac{1}{2}''$. The sensor element is mounted behind a 0.6" diameter opening on the rear side of the case, covered with wire mesh to protect the sensor and prevent ignition. A thick film sensor element of the type described hereinabove is mounted directly behind the opening. Output signal is displayed by a digital panel meter, such as an Acculex DP-176BL (Metrabyte, Taunton, Mass.), set for ±2 V full scale, mounted in the front of the case. Two 9 V dry cell batteries are used, one providing working voltage to the bridge circuit and the other providing power to operate the digital panel meter. The entire unit is portable and weighs less than 20 ounces.

The hydrogen detecting instrument described herein is particularly useful as a fast responding, portable device to detect hydrogen leaks in tanks and piping, and to detect a buildup of hydrogen in areas around batteries, plating tanks, furnaces, hydrogen production facilities, chemical processing facilities, etc.

The hydrogen detecting instrument described herein has certain advantages over that described in the parent patent application referenced hereinabove. The thick film device is less expensive to produce, and therefore more amenable to mass production. The thick film passivation layer is more impervious to hydrogen, more resistant to abrasion, and also more inert because of its greater thickness. Moreover, since the thick film device is sintered at high temperatures, it is useful at temperatures where thin films would tend to deteriorate.

While there has been shown and described what are at present considered the preferred embodiments of the invention, it will be obvious to those skilled in the art that various changes and modifications can be made therein without departing from the scope of the inventions defined by the appended claims.

What is claimed is:

1. A hydrogen sensor element comprising:
   an essentially inert, electrically-insulating substrate;
   a thick film metallization deposited on said substrate, said metallization forming at least two resistors on said substrate, said metallization comprising a sintered composition of Pd and a sinterable binder; and
   an essentially inert, electrically insulating, hydrogen impermeable passivation layer covering at least one of said resistors, at least one of said resistors being left uncovered, the difference in electrical resistances of said covered resistor and said uncovered resistor being related to hydrogen concentration in a gas to which said sensor element is exposed.

2. A hydrogen sensor element in accordance with claim 1 wherein said substrate comprises a material selected from the group consisting of silicon, glass, quartz, mica, ceramic, and porcelain enamel.

3. A hydrogen sensor element in accordance with claim 1 wherein said passivation layer comprises a sinterable material.

4. A hydrogen sensor element in accordance with claim 1 wherein said metallization comprises four resistors in a Wheatstone resistance bridge arrangement.

5. A hydrogen sensor element in accordance with claim 4 wherein each of said four resistors includes a secondary resistive element for allowing each of said four resistors to be trimmed in order to balance said Wheatstone resistance bridge arrangement.

6. A hydrogen sensor element in accordance with claim 4 wherein each of said four resistors includes an interconnective element.

7. A hydrogen sensor element in accordance with claim 1 wherein said Pd comprises a Pd alloy.

8. A hydrogen sensor element in accordance with claim 7 wherein said substrate comprises $Al_2O_3$, wherein said metallization comprises a sintered composition of a Pd-Ag alloy and glass frit, and wherein said passivation layer comprises a sintered dielectric glass-ceramic composition.

9. A hydrogen sensor element in accordance with claim 1 wherein each of said resistors has an aspect ratio of at least $L/W \cong 100$.

10. A hydrogen sensor element comprising:
    an essentially inert, electrically-insulating substrate;
    a thick film metallization deposited on said substrate, said metallization forming four resistors in a Wheatstone resistance bridge arrangement, said metallization comprising a sintered composition of Pd-Ag alloy and glass frit; and
    an essentially inert, electrically insulating, hydrogen impermeable passivation layer covering at least one of said resistors.

11. A hydrogen sensor element in accordance with claim 10 wherein said substrate comprises a material selected from the group consisting of silicon, glass, quartz, mica, ceramic, and porcelain enamel.

12. A hydrogen sensor element in accordance with claim 10 wherein said passivation layer comprises a sinterable material.

13. A hydrogen sensor element in accordance with claim 10 wherein each of said four resistors includes a secondary resistive element for allowing each of said four resistors to be trimmed in order to balance said Wheatstone resistance bridge arrangement.

14. A hydrogen sensor element in accordance with claim 10 wherein each of said four resistors includes an interconnective element.

15. An apparatus for detecting hydrogen comprising:
    a hydrogen sensor element comprising an essentially inert, electrically-insulating substrate; a thick film metallization deposited on said substrate, said metallization forming at least two resistors on said substrate, said metallization comprising a sintered composition of Pd or Pd alloy and a sinterable binder; and an essentially inert, electrically insulating, hydrogen impermeable passivation layer covering at least one of said resistors, said resistors forming at least part of a resistance bridge;

a power supply means for applying a fixed voltage to said resistance bridge; and a measuring means for detecting and measuring a voltage imbalance of said resistance bridge.

16. An apparatus in accordance with claim 15 wherein a plurality of said hydrogen sensor elements are distributed among various locations and communicate with a central instrument which monitors the outputs of said plurality of sensors and displays the hydrogen concentrations at said locations.

17. An apparatus in accordance with claim 15 wherein said measuring means further comprises means for providing indicia displaying said voltage imbalance as an indication of the presence of hydrogen.

18. A method of making a thick film hydrogen sensor comprising:

providing an essentially inert, electrically-insulating substrate;

depositing on said substrate a thick film metallization precursor, said metallization precursor forming at least two resistors on said substrate, said metallization precursor comprising a composition of Pd and a sinterable binder;

sintering said metallization precursor; and, depositing on said substrate an essentially inert, electrically insulating, hydrogen impermeable passivation layer covering at least one of said resistors, at least one of said resistors being left uncovered, the difference in electrical resistances of said covered resistor and said uncovered resistor being related to hydrogen concentration in a gas to which said sensor element is exposed.

19. A method in accordance with claim 18 further comprising:

depositing on said substrate a thick film metallization precursor, said metallization precursor forming a secondary resistive element of each of said resistors; and, sintering said metallization precursor.

20. A method in accordance with claim 18 further comprising:

depositing on said substrate a thick film metallization precursor, said metallization precursor forming an interconnective element of each of said resistors; and, sintering said metallization precursor.

* * * * *